United States Patent [19]

Anderson

[11] Patent Number: 5,150,707
[45] Date of Patent: Sep. 29, 1992

[54] ABSORBENT ASSEMBLY FOR USE AS A THERMAL PACK

[75] Inventor: Leslie B. Anderson, Easton, Pa.

[73] Assignee: Medico International, Inc., Palmer, Pa.

[21] Appl. No.: 539,841

[22] Filed: Jun. 18, 1990

[51] Int. Cl.⁵ ............................................... A61F 7/00
[52] U.S. Cl. .................... 128/402; 128/403; 604/368
[58] Field of Search ............ 128/379, 402, 403, 82.1, 128/400, 380, 399, 155, 156; 62/530, 3, 4; 604/368, 372; 53/428; 210/502.1; 34/95

[56] References Cited

U.S. PATENT DOCUMENTS

| | | |
|---|---|---|
| 370,730 | 9/1887 | Cussen . |
| 1,482,626 | 2/1924 | Whiting . |
| 1,561,650 | 11/1925 | Lashar . |
| 2,417,924 | 3/1947 | Gary . |
| 3,326,810 | 6/1967 | Dolan et al. . |
| 3,903,889 | 9/1975 | Torr .................................. 604/368 |
| 3,990,872 | 11/1976 | Cullen . |
| 4,205,674 | 6/1980 | Porat ................................. 128/156 |
| 4,454,055 | 6/1984 | Richman et al. ................. 128/156 |
| 4,464,443 | 8/1984 | Farrell et al. . |
| 4,519,798 | 5/1985 | Dinius .............................. 128/156 |
| 4,588,505 | 5/1986 | Walley et al. .................. 210/502.1 |
| 4,637,197 | 1/1987 | Banfield ............................ 53/428 |
| 4,645,698 | 2/1987 | Matsubara ........................ 604/368 |
| 4,655,209 | 4/1987 | Scott ................................ 128/156 |
| 4,673,402 | 6/1987 | Weisman et al. . |
| 4,686,776 | 8/1987 | Matsubara ........................... 34/95 |
| 4,688,572 | 8/1987 | Hubbard et al. ................. 128/802 |
| 4,802,574 | 2/1989 | Akiba ............................... 206/204 |
| 4,908,248 | 3/1990 | Nakashima et al. ............. 128/402 |

*Primary Examiner*—William H. Grieb
*Assistant Examiner*—Mark S. Graham
*Attorney, Agent, or Firm*—Dann, Dorfman, Herrell and Skillman

[57] ABSTRACT

A thermal pack having a high heat-retention character which may be quickly heated or chilled consisting of an absorbent package having a gel-forming synthetic organic resin in particulate form deposited on an adhesive-coated substrate disposed between a pair of fibrous non-woven porous filter layers and covered on the outside by a pair of paper-like plies of non-woven porous absorbent material. The outside covers are seamed together around their periphery to form a closed envelope.

The thermal pack of the present invention may be positioned in a pouch which is adapted to be held in place over the afflicted area of the body by releasable fastening means. The pack and pouch are formed of porous material which is capable of being heated in microwave oven or cooled in a freezer.

In making the absorbent pack, a predetermined quantity of particulate gel-forming resinous material is deposited on the adhesive surface of the substrate, which is water-soluble so that in use, when the assembly is immersed in water, the gel-forming synthetic organic resinous material is free to expand as a gel and fill the envelope provided by the peripheral seaming.

20 Claims, 2 Drawing Sheets

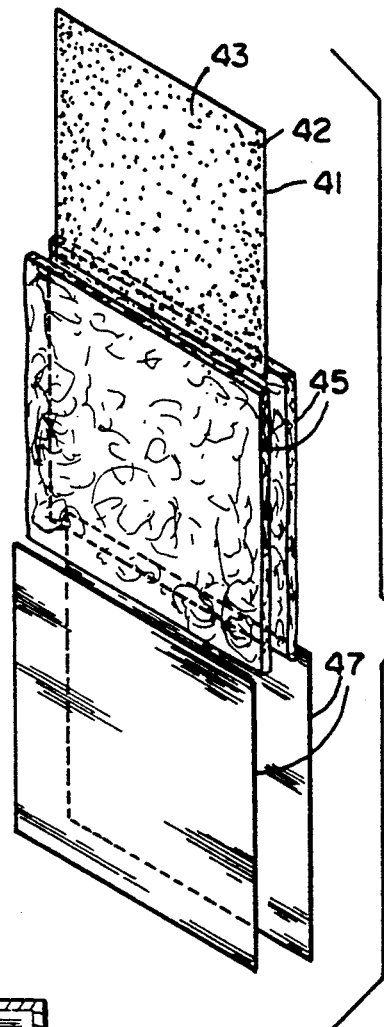
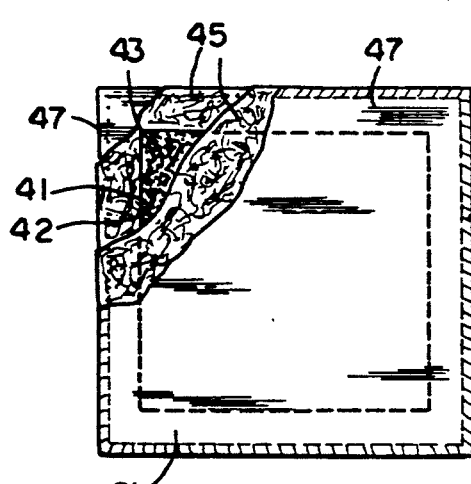
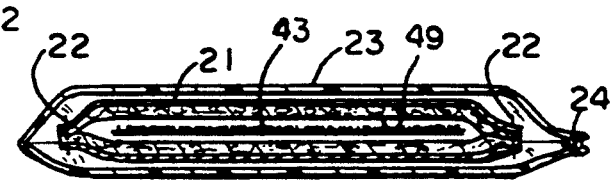
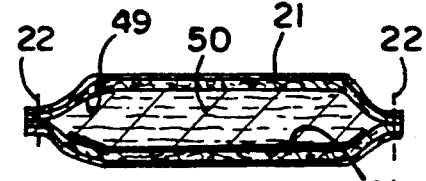

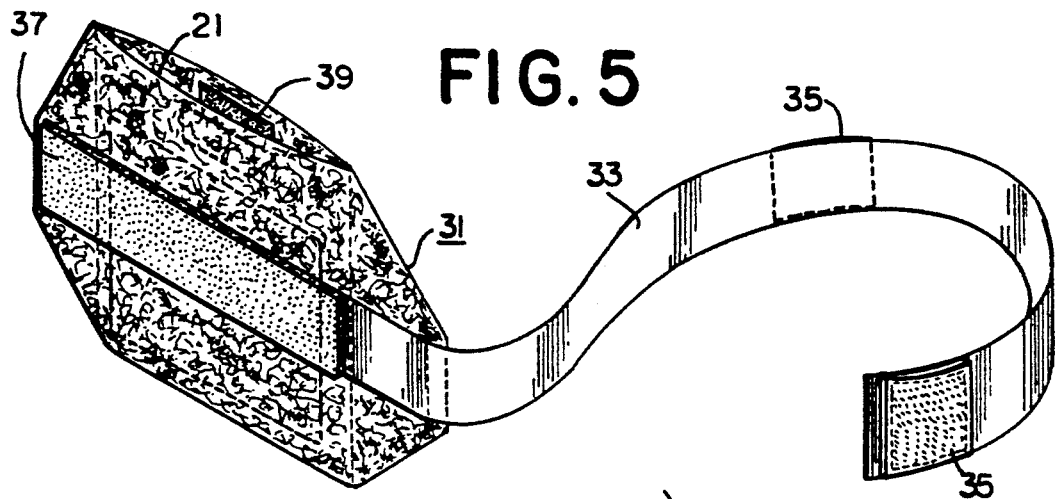
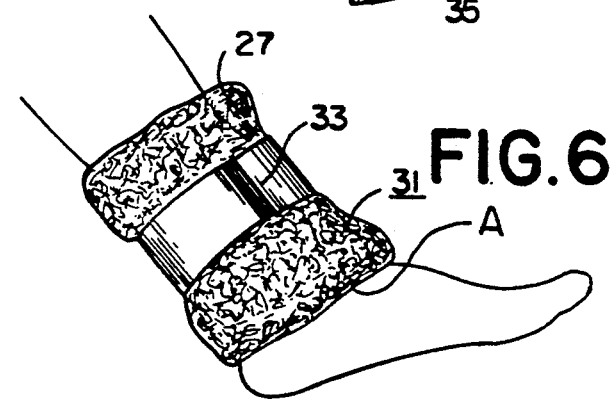
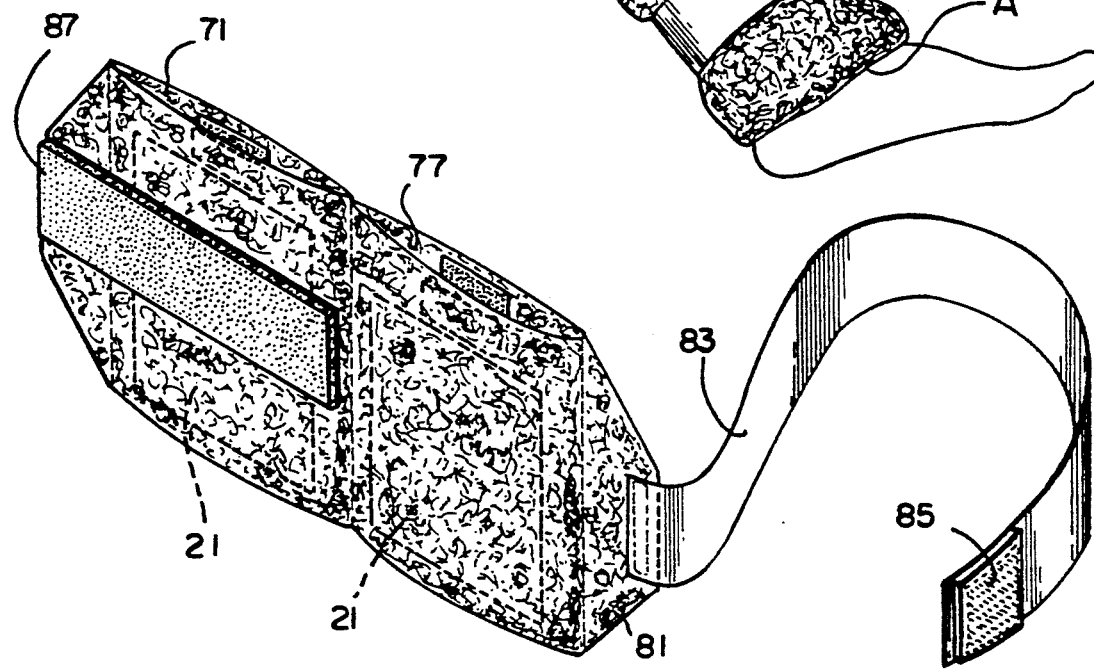

ABSORBENT ASSEMBLY FOR USE AS A THERMAL PACK

FIELD OF THE INVENTION

The present invention relates to absorbent package, and has particular application to an absorbent package which may be used in heat-and-chill therapy as a hot pack or cold pack for heat transfer, also referred to as a thermal pack.

BACKGROUND OF THE INVENTION

The most common thermal pack is a rubberized container for holding hot water or ice. The hot-water bottle or ice bag, as the case may be, is applied to afflicted body parts to apply heat or cold, as prescribed. Traditionally, the hot water bottle or ice bag is a rubber or rubber-like bladder which sheds water and dry heat transfer is accomplished. When moist heat or moist coolness is required, a moist towel is wrapped around the bladder. The towel provides the moist heat transfer but also reduces the efficiency of the heat transfer.

In recent years, the devices have been modified by the use of a rubberized fabric which has limited moisture retention properties and enables the utilization of moist heat transfer for a limited period, for example until the moisture in the fabric evaporates. The moisture-retention ability of the fabric is limited since the fabric must be impermeable to avoid leaking, and the moisture is retained on the outer surface of the fabric primarily by capillary attraction or by wicking.

SUMMARY OF THE PRESENT INVENTION

The present invention provides a thermal pack in which the heat transfer medium includes a body of a synthetic resin which forms a gel when exposed to water and will retain up to 200 times its dry weight of water. The gel is confined in a porous envelope which absorbs moisture from the gel and retains a moist condition after a prolonged time period.

The present invention also provides a novel method of making an absorbent pack which provides a proper distribution of a gel-forming resin within a porous envelope so as to enable a uniform exposure of the gel-forming resin to moisture so as to quickly obtain a body of gel encased in an envelope which confines the gel and enables facile handling of the package.

The present invention provides a thermal pack having a high heat-retention character which may be quickly heated or chilled in which the major component is simple water and yet which is bound in the pack so that it is not subject to rapid evaporation and cooling by evaporation, as would be case if the water were entirely free and unbound.

More specifically, the present invention provides an absorbent package having a gel-forming synthetic organic resin in particulate form deposited on an adhesive-coated substrate to obtain a substantially uniform distribution of the particulate material across the entire adhesive surface of the substrate in a relatively uniform layer. The layered substrate is then disposed between a pair of fibrous non-woven filter layers provided by absorbent batts on opposite sides of the coated substrate and the absorbent batts are covered on the outside by a pair of paper-like plies of non-woven porous absorbent material.

The thermal pack of the present invention may be positioned in a pouch which is adapted to be held in place over the afflicted area of the body by releasable fastening means such as Velcro, the pack and pouch being formed of material which is capable of being placed in microwave oven for elevating the temperature of the thermal pack or placed in a freezer for reducing the temperature.

In making the absorbent pack of the present invention, a predetermined quantity of particulate gel-forming resinous material is selected by depositing a uniform layer of the particulate material on the tacky adhesive surface of a substrate, and this substrate forms the central layer of a five-layered structure which is seamed around the outer periphery to form a closed envelope.

In the preferred form of the invention, the adhesive layer on the substrate is water-soluble so that when the assembly is immersed in water, the adhesive bond of the gel-forming synthetic organic resinous material to the substrate is freed so as to permit the gel-forming material to expand and fill the envelope provided by the peripheral seaming.

BRIEF DESCRIPTION OF THE DRAWINGS

All of the objects of the invention are more fully set forth hereinafter with reference to the accompanying drawings, wherein:

FIG. 1 is an expanded view showing the assembly of the absorbent pad which forms the thermal pack of the present invention;

FIG. 2 is a face view of the assembly after seaming around the margin, with portions broken away to illustrate its construction;

FIG. 3 is a transverse sectional view of the assembly enclosed in a sealed package;

FIG. 4 is a view of the assembly removed from the package and after immersion to expand the gel-forming resinous material within the envelope to form the thermal pack;

FIG. 5 is a perspective view of a pocketed holder for the thermal pack;

FIG. 6 is a thumbnail sketch showing the holder of FIG. 5 applied to an ankle; and FIG. 7 is a view similar to FIG. 5 of a second embodiment of holder for holding two thermal packs side by side.

DESCRIPTION OF THE PREFERRED EMBODIMENTS

The present invention provides a hot/cold compress which is designed for application to any afflicted part of the body. The product is available in one size for application to the limbs or other extremities of an adult and also may be used for application to small torsos. A larger size is available for application to adult torsos and other large body areas. The hot/cold compress comprises a holder which is adapted to encircle the afflicted part of the body and one or more absorbent pads or thermal packs adapted to be inserted into the holder to apply heat or cold to the afflicted body part.

The thermal pack comprises a pad which is fabricated and assembled in dry state as a relatively flat lightweight envelope. The pack includes a gel-forming acrylic resin which, when soaked in water, expands substantially, absorbing many times its dry weight so as to form a thick jelly-like mass within the thermal pack. The gel exhibits high heat-retention properties, and the moisture in the gel does not readily evaporate. The envelope of the thermal pack is porous so that the water may readily penetrate to the gel-forming material when the thermal pack is initially wetted through, and the porous nature of the envelope maintains the exposed surface of the thermal pack moist so as to facilitate heat transfer from the gel inside the envelope through the envelope and/or the holder to the outer surface where it may contact the afflicted body part to which the heat or cold should be applied.

The thermal pad is shown at 21 in FIGS. 1-5 and 7 and comprises a multi-layer assembly which is seamed about its periphery as indicated at 22. In the present instance, the seam comprises an overlaid blanket stitch about the perimeter of the pack. The pack is provided with a moisture-proof package 23 having a resealable closure 24, as shown in FIG. 3. The sealed package 23 prevents inadvertent absorption of water by reducing the tendency of the package to absorb moisture from the air when the pack is dry and flat as shown in FIG. 3. By the use of the resealable closure, the package 23 may also be used to store the thermal pack when swollen and wet (as shown in FIG. 4) to reduce the loss of moisture from the thermal pack, for example when it is desired to use dry heat or dry cold on an afflicted body part. Preferably, the package comprises a plastic bag which has an opening at one end, the open end including a releaseable and repetitively resealable seal of the type used in freezer storage bags.

In normal use, the thermal pack 21 is used in wet conditions outside of the package so that the moisture in the thermal pack serves to provide moist heat or moist cold to the afflicted body part. To this end, the thermal pack is preferably soaked, for example for two minutes in warm water, and then inserted in a holder 31 having a pocket 27 in which the thermal pack may be placed. The assembly may be heated in a microwave oven or chilled in a refrigerator or freezer to provide the desired heat sink. The pocket 27 is formed at one end of the holder 31 and the other end of the holder comprises an elastic strap 33 attached to the pocket and extending outwardly therefrom and terminating at its remote end in a pair of hook-type fasteners 35,35 positioned at spaced locations along the length of the elastic strap 33. A complementary loop fastener is provided on the holder 31 overlying the pocket 27 as indicated at 37 to cooperate with either or both of the hook fasteners 35. As shown in FIG. 6, the holder is adapted to be wrapped around a limb, for example an ankle A. The holder 31 with the thermal pack 21 in place within the pocket 27 is applied to the afflicted part of the limb and is held in place by wrapping the elastic strap around the limb to engage the hook fastener 35 with the loop fastener 37. The holder pocket 27 is preferably woven from a 100% cotton yarn so that it is readily washable and is capable of absorbing and holding the moisture when the moist thermal pack is positioned in the pocket. The moisture migrates into the terry cloth velour material of the pocket so as to apply moist heat or moist cold to the afflicted body part about which the holder is wrapped.

The thermal pack of the present invention is effective to absorb and retain moisture many times its dry weight. An operative material within the thermal pack comprises an absorbent hygroscopic or hydrophyllic material, preferably a material which forms a gel upon exposure to water. In the present instance, the material is a synthetic organic resin in particulate form, for example a crystalline acrylic resin which absorbs water up to 80 times its weight to form a gel in which the water is bound.

In fabricating the thermal pack 21, the hygroscopic gel-forming material is distributed across the full cross section of the pack. In the present instance, the distribution of the crystalline gel-forming substance is achieved with a square substrate film 41 having a tacky adhesive surface on one side. The tack level of the adhesive is such as to enable the crystalline gel-forming resinous substance to adhere to the tacky surface in a substantially uniform layer across the entire area of the substrate film 41. As shown in FIG. 1, the forward-facing surface 42 of the film is coated with adhesive. A layer 43 of crystalline gel-forming substance is deposited on the tacky adhesive surface. In the present case, the thickness of the deposited layer corresponds to the thickness of the crystals of the acrylic resin. The crystals are deposited in closely-abutting relation to completely cover the adhesive coating on the substrate 41. The adhesive, along with providing the proper tack level, is water soluble so that when the material 43 is exposed to water, the water will free the material from its temporary bond to the substrate 41 and allow the material to migrate away from the substrate to expand to the fullest extent possible. Preferably, the adhesive is of a composition which essentially dissolves within two minutes of its being contacted with water. As noted, the material, when subjected to water, forms a gel, and to prevent loss of the gel, the coated substrate 41 is positioned between a pair of filter layers 45 which permit the passage of liquid therethrough but confine the gel therebetween. In other words, the porosity of the layer 45 provides flow passages sufficiently large to pass water, but sufficiently small to block passage of gel therethrough. The filter material is in the form of a fibrous non-woven batt of an 80/20 blend of pulp and polypropylene on a tissue carrier sheet. In the present instance, the filter layer has a density of 3.9 ounces per square yard and is available as "Cyclean" filter media.

Layered onto the outside surfaces of the filter layers 45,45 are paper-like cover sheets 47, for example formed of a porous non-woven fabric consisting of 60% wood pulp and 40% polyester. The cover fabric may be, for example, two ounces per square yard and 14 mils thick. The cover sheet is a paper-like sheet which provides strength, abrasion resistance and absorbency. As shown in FIG. 2, the cover sheets 47 are mounted in registry with the filter layers 45 and the substrate 41 to form a five-layer assembly which is seamed around its outer periphery at 22 to form a closed envelope 49 for retaining the gel produced when the gel-forming substance 43 is exposed to water. As shown in FIG. 2, the seam is preferably formed by over-stitching extending about the perimeter of the layers 45 and 47. The stitching passes through the filter layers 45 and cover layers 47 but does not penetrate the substrate 41, so that the gel does not migrate outwardly through the seam. The gel is retained within the envelope 49 provided by the cover sheets 47 to provide a pillow effect as indicated at 50 in FIG. 3.

It is noted that the envelope 49, when the layer of material 43 is dry, has its layers directly superimposed on one another to provide a flat compact package which occupies minimal space and is relatively light in weight. The envelope 49 provides a hollow enclosure around the particulate material, and as shown in FIG. 4, this hollow enclosure expands in volume as the material 43 transforms from particulate into gel form, expanding several times its volume. In order to accommodate the expansion, the carrier film 41 is smaller in area than the layers 45 and 47 so that there are marginal areas around the four sides of the layers 45 and 47 which extend beyond the perimeter of the film 41. The seam 22 interconnects the layers 45 and 47 about their peripheries in this marginal portion so that the seam 22 is free to contract inwardly to enable expansion of the hollow enclosure formed by the envelope 49 to the pillow-like form shown in FIG. 4.

If it should be desired to anchor the film 41 into the seam 22, one edge of the film may be extended to the edge of the layers 45 and 47 so that the film is sewn into the seam along that edge. Anchoring one edge of the film in the seam does not detract from the ability of the envelope to expand the volume of the hollow enclosure. If the carrier film 41 is capable of shrinking upon becoming moist, all four sides of the film may be anchored in the seam 22. Similarly, if the layers 45 and 47 are stretchable, anchoring this film 41 in the seam will not adversely affect the expansion of the hollow enclosure when the material 43 is wetted. The gel confined within the expanded envelope 49 has a high heat-retention property and the manner of fabrication of the assembly enables the entire assembly to be heated in a microwave oven without damage to the oven or to the components of the assembly.

The use of the adhesive-coated substrate to meter the quantity of particulate gel-forming material has proved effective to assure that the quantity of gel substantially fills the expanded envelope 49 without creating undue pressure tending to express the gel outwardly through the seam or through the filter layers 45. The crystalline gel-forming material is deposited in a single layer on the substrate 41 by the adhesive surface, and a single layer on the order of 16 to 20 square inches is effective to absorb almost a full pound of water. The quantity of gel-forming material may be immersed or decreased by increasing or decreasing the area of the adhesive surface. For example, if an increase in the quantity is required, both sides of the carrier film may be adhesive to provide a layer of material on each side of the film. Since the water is absorbed to form the gel, it is bound into the gel and is not readily evaporated from the gel so as to retain the moistness. The moist nature of the thermal pack when positioned in the holder 31 dampens the holder to provide a dampness which assists in the transfer of heat between the thermal pack and the afflicted body part.

If it is desired to avoid dampening the afflicted body part, for example when the part is freshly bandaged, the moistness of the thermal pack may be confined by placing the expanded pack into the package 23 and closing the seal 24. Preferably, the pack is heated or cooled before the package 23 is sealed. The sealed package may then be placed in a holder 31 and used to provide dry heat or dry cool to the afflicted body part.

When used as a compress, the gel-like character of the pack enables it to conform to the contour of the afflicted body part to provide intimate contact and therefore good heat transfer between the afflicted body part and the thermal pack. If desired to use the thermal pack as an ice pack, the gel may be molded and frozen to conform to the shape of the body part to which it is to be applied and when frozen, will provide the desired cold pack conforming to the contour of the afflicted body part.

The pack may also be used with a modified holder as shown in FIG. 7 where two thermal packs are mounted in a holder 81 having a pair of pockets 77,77, each of which may hold a thermal pack. The holder 81 has a strap 83 attached to it with suitable hook fasteners 85 adjacent the free end thereof. The holder 81 also mounts a loop fastener 87 to cooperate with the hook fastener 85 to enable the pack to be applied to an afflicted body portion. If the elastic strap 83 is not sufficiently long to encircle the girth of the body portion, an extender strap (not shown) having hook fasteners at one end and loop fasteners at the other end may be connected to the strap 83 to effectively lengthen the elastic strap 83.

While particular embodiments of the present invention have been herein illustrated and described, it is not intended to limit the invention to such disclosures, but changes and modifications may be made therein and thereto within the scope of the following claims.

I claim:

1. A hot/cold compress for application to an afflicted body portion comprising at least two thermal packs and a holder having at least two pockets disposed side-by-side for receiving said thermal packs, at least one in each pocket, and a strap adapted to encircle said body portion attached at one end to one by said pocket and having releasable fastening means to releasably engage said holder adjacent said pockets, each said thermal pack comprising an absorbent assembly of hydrophilic material comprising a carrier film having a layer of water-soluble adhesive material on at least one surface thereof, a layer of hydrophilic particulate material adhered to said carrier film by said adhesive layer, said particulate hydrophilic material operable upon contact with water to expand in the form of a gel, said carrier film and said particulate material adhered thereto forming the central layer of a multi-layer package, the outer layers of said multi-layer package comprising porous material having flow passages therethrough of a size sufficiently large to afford migration of water through the pores from outside the package into the central layer, and vice versa, and sufficiently small to restrict migration of the gel from the central layer outwardly through the outer layers, said outer layers having a seam extending around their periphery to form a hollow enclosure surrounding said carrier film, said hollow enclosure adapted to be expanded to accommodate the expansion of said particulate material caused by forming a gel upon contact with water, whereby upon contacting said assembly with water, water migrates through said outer layers into said enclosure to cause said particulate matter to form a gel and also to dissolve the adhesive material to free said particulate matter and the gel from adherence to said carrier film.

2. A compress according to claim 1 wherein said pockets are formed of a cotton fabric and said strap is elastic to hold said pockets compressed against the afflicted body portion.

3. A hot/cold compress for application to an afflicted body portion comprising a thermal pack, a resealable package enclosing said pack to provide a moisture barrier, and a holder having a pocket for receiving said thermal pack and a strap adapted to encircle said body portion attached at one end to said pockets and having releasable fastening means to releasably engage said pocket,
- said thermal pack comprising an absorbent assembly of hydrophilic material comprising a carrier film having a layer of water-soluble adhesive material on at least one surface thereof, a layer of hydrophilic particulate material adhered to said carrier film by said adhesive layer, said particulate hydrophilic material operable upon contact with water to expand in the form of a gel,
- said carrier film and said particulate material adhered thereto forming the central layer of a multi-layer package, the outer layers of said multi-layer package comprising porous material having flow passages therethrough of a size sufficiently large to afford migration of water through the pores from outside the package into the central layer and sufficiently small to restrict migration of the gel from the central layer outwardly through the outer layers,
- said outer layers having a seam extending around their periphery to form a hollow enclosure surrounding said carrier film, said hollow enclosure adapted to be expanded to accommodate the expansion of said particulate material caused by forming a gel upon contact with water, whereby upon removal of said pack from said package and contacting said pack with water, water migrates through said outer layers into said enclosure to cause said particulate matter to form a gel and also to dissolve the adhesive material to free said particulate matter and the gel from adherence to said carrier film.

4. A compress according to claim 3 wherein said resealable package comprises a plastic bag having an opening with a repetitively resealable seal, said opening affording said removal of the pack from the package.

5. A compress according to claim 3 wherein said outer layers of the thermal pack comprise a cover layer exposed to ambient conditions and an intermediate layer between said cover layer and said film said cover layer comprising a fabric providing strength, abrasion resistance and absorbency and said intermediate layer comprising a filter layer providing said flow passages.

6. A compress according to claim 5 wherein said cover layer comprises a paper-like sheet of non-woven fabric and said intermediate layer comprises a non-woven batt of fibrous material.

7. A compress according to claim 3 wherein said gel-forming particulate material comprises a crystalline acrylic resin, and said water-soluble adhesive is of a composition which essentially dissolves within two minutes of its being contacted with water.

8. A compress according to claim 3 wherein said outer layers have an area larger than the area of the carrier film and extend beyond the carrier film to provide marginal portions on at least two sides beyond the edges to the carrier film, said seam being positioned in said marginal portions.

9. A compress according to claim 8 wherein said marginal portions extend beyond the film about the entire periphery of the film.

10. A compress according to claim 3 wherein the multiple layers of said thermal pack in a dry state are superimposed directly upon one another to form a flat compact pack for storage prior to use.

11. A compress according to claim 3 wherein said pocket is formed of a cotton fabric and said strap is elastic to hold said pocket compressed against the afflicted body portion.

12. An absorbent assembly of hydrophilic material comprising a carrier film having a layer of water-soluble adhesive material on at least one surface thereof, a layer of hydrophilic particulate material adhered to said carrier film by said adhesive layer, said particulate hydrophilic material operable upon contact with water to expand in the form of a gel, said carrier film and said particulate material adhered thereto forming the central layer of a multi-layer thermal pack, the outer layers of said thermal pack comprising porous material having pores of a size sufficiently large to afford migration of water through the pores from outside the pack into the central layer, and vice versa, and sufficiently small to restrict migration of the gel from the central layer outwardly through the outer layers, said outer layer having a seam extending around their periphery to form a hollow enclosure surrounding said carrier film, said hollow enclosure adapted to be expanded to accommodate the expansion of said particulate material caused by forming a gel upon contact with water, whereby upon contacting said assembly with water, water migrates through said outer layers into said enclosure to cause said particulate matter to form a gel and also to dissolve the adhesive material to free said particulate matter and the gel from adherence to said carrier film, and a resealable package enclosing said thermal pack to provide a moisture barrier preventing inadvertent absorption of water.

13. An assembly according to claim 12 wherein said resealable package comprises a plastic bag having an opening affording removal of said pack from the package, said opening having a repetitively resealable seal.

14. An assembly according to claim 12 wherein said outer layers of the pack comprise a cover layer exposed to ambient conditions when removed from the package and an intermediate layer between said cover layer and said film, said cover layer comprising a fabric providing strength, abrasion resistance and absorbency and said intermediate layer comprising a filter layer providing said flow passages, whereby ambient conditions may afford evaporation of moisture migrating from said gel outwardly through said intermediate layer.

15. An assembly according to claim 14 wherein said cover layer comprises a paper-like sheet of non-woven fabric and said intermediate layer comprises a non-woven batt of fibrous material.

16. An assembly according to claim 12 wherein said gel-forming particulate material comprises a crystalline acrylic resin, and said water-soluble adhesive is of a composition which essentially dissolves within two minutes of its being contacted with water.

17. An assembly according to claim 12 wherein said outer layers have an area larger than the area of the carrier film and extend beyond the carrier film to provide marginal portions on at least two sides beyond the edges of the carrier film, said seam being positioned in said marginal portions.

18. An assembly according to claim 17 wherein said marginal portions extend beyond the film about the entire periphery of the film.

19. An assembly according to claim 12 wherein the multiple layers of said assembly in a dry state are superimposed directly upon one another to form a flat compact pack for storage prior to use.

20. An absorbent assembly of hydrophilic material comprising a thin compact carrier film having a layer of water-soluble adhesive material on at least one surface thereof, a layer of hydrophilic crystalline material adhered in a single layer to said at least one surface of said carrier film by said adhesive layer, said particulate hydrophilic material operable upon contact with water to expand in the form of a gel, said carrier film and said particulate material adhered thereto forming the central layer of a multi-layer thermal pack, the outer layers of said pack comprising porous material having pores of a size sufficiently large to afford migration of water through the pores from outside the package into the central layer, and vice versa, migration of moisture through the pores and evaporation of the moisture from the outer layers and of a size sufficiently small to restrict migration of the gel from the central layer outwardly through the outer layers, said outer layers having a seam extending around their periphery to form a hollow enclosure surrounding said carrier film, said hollow enclosure adapted to be expanded to accommodate the expansion of said particulate material caused by forming a gel upon contact with water, whereby upon contacting said assembly with water, water migrates through said outer layers into said enclosure to cause said particulate matter to form a gel and also to dissolve the adhesive material to free said particulate matter and the gel from adherence to said carrier film.

* * * * *

UNITED STATES PATENT AND TRADEMARK OFFICE
CERTIFICATE OF CORRECTION

PATENT NO. : 5,150,707
DATED : September 29, 1992
INVENTOR(S) : Leslie B. Anderson It is certified that error appears in the above-identified patent and that said Letters Patent is hereby corrected as shown below:

Column 6, line 26, "by said pocket" should be --of said pockets--;

line 68, "pockets" should be --pocket--;

Column 8, line 17, "layer" should be --layers--.

Signed and Sealed this

Twenty-sixth Day of October, 1993

Attest:

BRUCE LEHMAN

*Attesting Officer*    *Commissioner of Patents and Trademarks*